(12) United States Patent
Goebbel et al.

(10) Patent No.: US 7,786,317 B2
(45) Date of Patent: Aug. 31, 2010

(54) PROCESS FOR EPOXIDIZING PROPENE

(75) Inventors: Hans-Georg Goebbel, Kallstadt (DE); Peter Bassler, Viernheim (DE); Joaquim Henrique Teles, Otterstadt (DE); Peter Rudolf, Ladenburg (DE); Ulrich Mueller, Neustadt (DE); Anna Forlin, Vigonza (IT); Malte Schulz, Hollern-Tw. (DE); Meinolf Weidenbach, Drochtersen (DE)

(73) Assignees: BASF Aktiengesellschaft, Ludwigshafen (DE); The Dow Chemical Company, Midland, MI (US)

( * ) Notice: Subject to any disclaimer, the term of this patent is extended or adjusted under 35 U.S.C. 154(b) by 19 days.

(21) Appl. No.: 12/159,404

(22) PCT Filed: Dec. 18, 2006

(86) PCT No.: PCT/EP2006/069865
§ 371 (c)(1),
(2), (4) Date: Jun. 27, 2008

(87) PCT Pub. No.: WO2007/074101
PCT Pub. Date: Jul. 5, 2007

(65) Prior Publication Data
US 2008/0306290 A1    Dec. 11, 2008

Related U.S. Application Data

(60) Provisional application No. 60/775,780, filed on Feb. 23, 2006.

(30) Foreign Application Priority Data
Dec. 27, 2005  (IT) ........................ MI2005A2491

(51) Int. Cl.
*C07D 301/12*    (2006.01)
(52) U.S. Cl. ..................................... 549/531
(58) Field of Classification Search ................. 549/531
See application file for complete search history.

(56) References Cited

U.S. PATENT DOCUMENTS

| 3,477,919 A | 11/1969 | Lichtenwalter et al. |
| 3,816,478 A | 6/1974 | Washall et al. |
| 4,691,034 A | 9/1987 | Sanderson et al. |
| 5,214,168 A * | 5/1993 | Zajacek et al. ............ 549/531 |
| 5,397,475 A | 3/1995 | Millar et al. |
| 5,866,734 A | 2/1999 | Flick et al. |
| 5,932,187 A | 8/1999 | Ledon et al. |
| 6,380,119 B1 | 4/2002 | Grosh et al. |
| 2004/0068128 A1 | 4/2004 | Teles et al. |
| 2005/0252762 A1 | 11/2005 | Bassler et al. |
| 2005/0258026 A1 | 11/2005 | Bassler et al. |

FOREIGN PATENT DOCUMENTS

| DE | 4222109 | 1/1994 |
| EP | 0200260 | 12/1986 |
| EP | 0311983 | 4/1989 |
| EP | 0405978 | 1/1991 |
| EP | 0827944 | 3/1998 |
| EP | 1359148 | 11/2003 |
| EP | 1424332 | 6/2004 |
| WO | 98/55228 | 12/1998 |
| WO | 99/26937 | 6/1999 |
| WO | 02/14298 | 2/2002 |
| WO | 2004/009566 | 1/2004 |
| WO | 2004/009567 | 1/2004 |
| WO | 2004/074268 | 9/2004 |

OTHER PUBLICATIONS

Ullmann's Encyclopedia of Industrial Chemistry, "Antidiabetic Drugs to Benzoquinone and Naphthoquinone Dyes", 5th Edition, vol. 3, 1989, pp. 447-457.
Ullmann's Encyclopedia of Industrial Chemistry, "High-Perfomance Fibers to Imidazole and Derivatives", 5th Edition, vol. 13, pp. 447-456, 1985.
U.S. Appl. No. 12/597,616, filed Oct. 26, 2009, Schubert, et al.

* cited by examiner

*Primary Examiner*—Janet L Andres
*Assistant Examiner*—David E Gallis
(74) *Attorney, Agent, or Firm*—Oblon, Spivak, McClelland, Maier & Neustadt, L.L.P.

(57) ABSTRACT

The present invention provides a process for the epoxidation of propene which comprises reacting propene with hydrogen peroxide in the presence of methanol as solvent and a titanium zeolite catalyst, the process further comprising separating propylene oxide from the reaction mixture to obtain a mixture comprising methanol, water, at least one carboxylic acid and at least one carbonyl compound, wherein the at least one carboxylic acid is at least partially neutralized, said process optionally comprising a hydrogenation stage.

22 Claims, No Drawings

PROCESS FOR EPOXIDIZING PROPENE

FIELD OF THE INVENTION

The present invention provides a process for the epoxidation of propene which comprises reacting propene with hydrogen peroxide in the presence of methanol as solvent and a titanium zeolite catalyst and separating propylene oxide from the resulting reaction mixture to obtain a mixture (Ma) comprising methanol, water, at least one carboxylic acid having from 1 to 3 carbon atoms and at least one carbonyl compound having from 1 to 3 carbon atoms, wherein the carbonyl compound is an aldehyde or a ketone. Said process further comprises at least partially neutralizing the at least one carboxylic acid comprised in mixture (Ma) by adding a base to mixture (Ma) to obtain a mixture (Mb) and separating methanol from mixture (Mb) by distillation wherein the methanol obtained is at least partially recycled as solvent into the epoxidation reaction. Optionally, mixture (Ma) is subjected to catalytic hydrogenation prior to neutralisation. Moreover, the present invention also relates to process for the purification of methanol which process comprises at least partially neutralizing at least one carboxylic acid having from 1 to 3 carbon atoms comprised in a mixture (Ma) by adding a base to mixture (Ma) to obtain a mixture (Mb), said mixture (Ma) further comprising methanol, water and at least one carbonyl compound having from 1 to 3 carbon atoms, wherein the carbonyl compound is an aldehyde or a ketone, said process further comprising separating methanol from mixture (Mb) by distillation.

BACKGROUND OF THE INVENTION

In numerous publications on the subject of the preparation of propylene oxide, there are only a few which are concerned with the purification of the solvent which is in most preferred cases methanol, and the re-use of this solvent in the epoxidation reaction.

EP 1 359 148 A1 describes a process in which, prior to separation of methanol from a mixture which essentially comprises methanol and water, the mixture is subjected to hydrogenation, and the resulting (hydrogenated mixture) is distilled to purify and afterwards re-use the solvent. As a preferred embodiment, this document of the prior art describes a process in which, after hydrogenation and prior to distillation, the pH of solvent stream to be purified is adjusted to values of below 7 using an acid such as sulfuric acid.

EP 1 424 332 A1 describes a process in which the crude propylene oxide resulting from an epoxidation reaction and to be purified is admixed with a compound containing an unsubstituted NH$_2$ group and which is capable of reacting with acetaldehyde. This mixture is subjected to extractive distillation to obtain purified propylene oxide. This document of the prior art also discloses an embodiment according to which the crude propylene oxide stream is mixed with an aqueous alkaline solution before feeding it to the extractive distillation column. According to the specific disclosure of this document, addition of this aqueous alkaline solution leads to the conversion of methyl formate to methanol and formate by hydrolysation.

WO 02/14298 A1 describes a process for the continuous preparation of an olefinic oxide by direct oxidation of an olefin with hydrogen peroxide which, among several other steps, a step (c) in which the tail product of a distillation zone and an aqueous basic solution are fed into a decomposition zone, wherein this zone contains a decomposition catalyst which decomposes hydrogen peroxide comprised in the tail product to oxygen and water. The aqueous basic solution is added in order to control the pH of the catalytically driven hydrogen peroxide decomposition reaction which must have values greater than 10.

WO 99/26937 A1 relates to removing oxygenate impurities from an organical chemical feed by treatment with an aqueous reducing agent and an aqueous base, accompanied by separation. It is disclosed that it is preferred that the aqueous base is introduced in a molar equivalent excess relative to the level of oxygenate impurities present. As preferred reducing agents, sulfurous acid, sodium hydrogen sulfite, sodium sulfite, sodium metabisulfite, sodium borohydride, and potassium borohydride and mixtures thereof are described. According to the most preferred embodiments, the streams which are treated by reducing agents and/or aqueous bases essentially consist of isobutane, propylene, propylene oxide and mixtures thereof, wherein this steams contain the oxygenate impurities. Therefore, for example, these streams are treated with aqueous base in order to remove the impurities from propylene oxide.

U.S. Pat. No. 4,691,034 relates to the purification of propylene oxide by treatment with calcium hydroxide in glycerol or sugar water. From such process, propylene oxide is obtained which is essentially free of methyl formate. Glycerol or sugar water are used as solubilizing agents to improve the solubility of calcium hydroxide. As in WO 99/26937 A1, the stream to be treated with base essentially consists of propylene oxide to be purified.

U.S. Pat. No. 3,477,919 which is cited in U.S. Pat. No. 4,691,034 relates to the use of calcium hydroxide slurry to remove methyl formate contaminant from propylene oxide prepared by the epoxidation of propylene with tertiary butyl hydroperoxide. In this process, the calcium hydroxide is used to produce methanol and the calcium salt of formic acid from methyl formate.

U.S. Pat. No. 3,816,478 relates to the purification of a material containing aldehyde impurities. Such materials are organic liquids containing small amounts of water. Treatment is carried out by passing the contaminated stream through a bed of sodium bisulfite as reducing agent.

US 2004/0068128 A1 discloses a process for the manufacturing of an epoxide which comprises reducing, preferably hydrogenating a mixture comprising alpha-hydroperoxy alcohols which are converted to propylene glycols. The reduced mixture is then subjected to a further step in which a solvent contained in the mixture is separated and, if desired, recirculated into the process.

It is an object of the present invention to provide a novel process for the epoxidation of propene which comprises the use of methanol as solvent and the recirculation of this solvent, which process allows for decreasing the content of the methanol regarding carbonyl compounds, particularly acetaldehyde, the methanol having a decreased content of carbonyl compounds preferably being recirculated as solvent in the epoxidation of propene.

It is yet another object of the present invention to provide work-up stages for reaction mixtures obtained from epoxidation reactions which allow for recirculation of a pure solvent used in the epoxidation reaction.

It is a further object of the present invention to provide a process for the purification of mixtures containing methanol and carbonyl compounds.

SUMMARY OF THE INVENTION

The present invention provides a process for the epoxidation of propene, comprising (a) reacting propene with hydrogen peroxide in the presence of methanol as solvent and a titanium zeolite catalyst and separating propylene oxide from the resulting reaction mixture to obtain a mixture (Ma) comprising methanol, water, at least one carboxylic acid having from 1 to 3 carbon atoms and at least one carbonyl compound having from 1 to 3 carbon atoms, wherein the carbonyl compound is an aldehyde or a ketone;
(b) at least partially neutralizing the at least one carboxylic acid comprised in mixture (Ma) by adding a base to mixture (Ma) to obtain a mixture (Mb);
(c) separating methanol from mixture (Mb) by distillation;
(d) at least partially recycling the methanol obtained from (c) into (a).

The present invention also provides a process for the epoxidation of propene, comprising
(a) reacting propene with hydrogen peroxide in the presence of methanol as solvent and a titanium zeolite catalyst and separating propylene oxide from the resulting reaction mixture to obtain a mixture (Ma) comprising from 55 to 85 wt.-% methanol, from 10 to 40 wt.-% water, from 0.001 to 0.5 wt.-% of at least one carboxylic acid having from 1 to 3 carbon atoms and from wherein the at least one carboxylic acid is selected from the group consisting of formic acid, acetic acid, propionic acid, and a mixture of two or more thereof, and wherein the at least one carbonyl compound is selected from the group consisting of formaldehyde, acetaldehyde, propionaldehyde, and a mixture of two or more thereof;
  said mixture (Ma) further comprising from 0.1 to 1 wt.-% of 2-hydroperoxypropanol-1, 1-hydroperoxypropanol-2 or a mixture of 2-hydroperoxypropanol-1 and 1-hydroperoxypropanol-2; and
  subjecting mixture (Ma) to catalytic hydrogenation at a temperature of from 65 to 85° C. and at a hydrogen partial pressure of from 3 to 20 bar, preferably of from 3 to 13 bar, to give a mixture comprising from 0.1 to 1.3 wt.-% 1,2-dihydroxypropane, the hydrogenation catalyst comprising a catalytically active metal selected from the group consisting of Pd, Pt, Rh, Ir, Os and a mixture of two or more thereof;
(b) at least partially neutralizing the at least one carboxylic acid comprised in the mixture obtained from catalytic hydrogenation by adding an aqueous solution comprising hydroxide ions to this mixture to obtain a mixture (Mb) which contains at least one compound having a boiling temperature lower than methanol and lower than water and which is selected from the group consisting of formaldehyde, acetaldehyde, propionaldehyde, methyl formate, formaldehyde dimethyl acetal, acetaldehyde dimethyl acetal, and a mixture of two or more thereof at a given pressure, wherein the molar ratio of hydroxide ions introduced relative to carboxylic acid comprised in the mixture obtained from catalytic hydrogenation is from 0.1 to 10;
(c) separating methanol from mixture (Mb) by
  (c1) separating the at least one compound having a boiling temperature lower than methanol and lower than water from mixture (Mb) by distillation at a distillation pressure of from 0.5 to 2 bar to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises from 5 to 50 wt.-% methanol and at least 0.1 wt.-% of the at least one compound having a boiling point lower than methanol and water;
  (c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising 1,2-dihydroxypropane and at least 90 wt.-% of water,
(d) at least partially recycling the methanol obtained from (c2) into (a), the methanol comprising not more than 200 ppm of carbonyl compounds,
(e) separating 1,2-dihydroxypropane from mixture (Mc2ii).

The present invention also provides a process for the purification of methanol, comprising at least partially neutralizing at least one carboxylic acid having from 1 to 3 carbon atoms comprised in a mixture (Ma) by adding a base to mixture (Ma) to obtain a mixture (Mb), said mixture (Ma) further comprising methanol, water and at least one carbonyl compound having from 1 to 3 carbon atoms, wherein the carbonyl compound is an aldehyde or a ketone, said process further comprising separating methanol from mixture (Mb) by distillation.

DETAILED DESCRIPTION OF THE INVENTION

According to the present invention, propene is reacted with hydrogen peroxide in the presence of methanol as solvent and a titanium zeolite catalyst in stage (a). Additionally, propylene oxide is separated from the reaction mixture resulting from the epoxidation reaction wherefrom a mixture (Ma) is obtained which comprises methanol, water, at least one carboxylic acid having from 1 to 3 carbon atoms and at least one carbonyl compound having from 1 to 3 carbon atoms, wherein the carbonyl compound is an aldehyde or a ketone.

Stage (a)

The epoxidation reaction of stage (a) of the inventive process is carried out in methanol as solvent. Optionally, a solvent mixture comprising methanol and at least one other suitable solvent can be employed. Preferably, a solvent mixture of methanol and water is used. If the epoxidation reaction is carried out in a solvent mixture comprising water, the water may be introduced as such and/or via, e.g., an aqueous hydrogen peroxide solution.

The reaction according to stage (a) can be conducted in one, two, three or more stages. Preferably, the reaction is conducted in one, two or three stages, more preferably in one or two stages and especially preferably in two stages.

Therefore, the present invention also relates to a process as described above, wherein in (a), propene is reacted with hydrogen peroxide in the presence of a titanium zeolite catalyst to give a mixture comprising propylene oxide, methanol, and water.

According to a still further preferred embodiment, the inventive process comprises in (a) at least one, such as one, two, three or more, preferably one or two, still more preferably one intermediate separation stage between two subsequent reaction stages. According to a still further preferred embodiment, unreacted propene is separated in at least one separation stage.

Therefore, the inventive process comprises in (a) at least the following sequence of stages (i) to (iii):
(i) reaction of propene with hydrogen peroxide in the presence of a titanium zeolite catalyst to give a mixture comprising propylene oxide, unreacted propene, methanol and water;
(ii) separation of the unreacted propene from the mixture resulting from stage (i), (iii) reaction of the propene which has been separated off in stage (ii) with hydrogen peroxide.

Therefore, stage (a) of the inventive process can comprise, in addition to stages (i) and (iii), at least one further reaction stage and, in addition to stage (ii), at least one further separation stage.

As to stages (i) and (iii), there are no specific restrictions as to how the reaction is carried out.

Accordingly, it is possible to carry out one of the reactions stages in batch mode or in semi-continuous mode or in continuous mode and independently thereof, the other reaction stage in batch mode or in semi-continuous mode or in continuous mode. According to an even more preferred embodiment, both reaction stages (i) and (iii) are carried out in continuous mode.

The epoxidation reaction in stages (i) and (iii) is preferably carried out in the presence of at least one titanium zeolite catalyst.

Zeolites are, as is known, crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminum is present and in which part of the Si(IV) in the silicate lattice is replaced by titanium as Ti(IV) are known. These titanium zeolites, in particular those having a crystal structure of the MFI type, and possible ways of preparing them are described, for example, in WO 98/55228, EP 0 311 983 A2, EP 0 405 978 A1, or EP 0 200 260 A2. Apart from silicon and titanium, such materials can further comprise additional elements such as aluminum, zirconium, tin, iron, cobalt, nickel, gallium, germanium, boron or small amounts of fluorine.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YNU, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", TS-3", and also Ti zeolites having a framework structure isomorphous with beta-zeolite. Very particular preference is given to using zeolite catalysts of the TS-1 structure and the Ti-MWW structure, particularly to using zeolite catalysts of structure TS-1.

The titanium zeolite catalysts and still more preferably the titanium zeolite catalysts having TS-1 or MWW structure, can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates, it is preferred to cut the extrudates with a stream essentially consisting of an inert gas.

Most preferably, a TS-1 or Ti-MWW catalyst is employed which is produced by first forming microspheres, for example microspheres formed according to EP 0 200 260 A2, and then forming said microspheres to obtain shaped bodies, preferably extrudates as described above.

For each of these forming or shaping methods according to which catalyst powder is processed to give shaped bodies such as microspheres, extrudates, granules, pellets, and the like, it is possible to use at least one additional binder and/or at least one pasting agent and/or at least one pore forming agent. Prior to using the catalyst in the epoxidation reaction of the present invention, it is possible to suitably pretreat the catalyst. In case the catalyst is used as supported catalyst, carriers can be preferably used which are inert, i.e. which do not react with hydrogen peroxide, olefin, and olefin oxide.

The reactions in stages (i) and (iii) are preferably carried out in suspension mode or fixed-bed mode, most preferably in fixed-bed mode.

In the inventive process, it is possible to use the same or different types of reactors in stages (i) and (iii). Thus, it is possible to carry out one of the reaction stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors, wherein at least two reactors are serially coupled and wherein at least two reactors are operated in parallel. According to a preferred embodiment, stage (i) of the present invention is carried out in at least two reactors which are operated in parallel, and stage (iii) of the present invention is carried out in a single reactor.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to choose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors in stage (i) and at least one reactor in stage (iii). According to a still further embodiment, the at least two reactors used in stage (i) are serially connected or operated in parallel, more preferably operated in parallel. Generally, it is necessary to equip at least one of the reactors used in stage (i) and/or (iii) with a cooling means such as a cooling jacket in order to remove at least partially the heat resulting from reaction in the respective reactor. Especially preferably, at least two reactors are employed in stage (i) which are connected in parallel and can be operated alternately. In case the reactors are operated in upflow mode, the two or more reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20 000, preferably from 10 to 10 000, more preferably from 100 to 9000, more preferably from 1000 to 8000 and particularly preferably from 3000 to 7000, tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

In stage (iii), particular preference is given to using a shaft reactor, more preferably a continuously operated shaft reactor and particularly preferably a continuously operated, adiabatic shaft reactor. According to the present invention, it is also possible to use two or more of these reactors such as two, three or four of these reactors which are serially coupled or coupled in parallel, more preferably in parallel.

Therefore, the present invention also relates to a process as described above wherein in stage (i), at least two shell-and-tube reactors each having of from 1 to 20.000 internal tubes and being continuously operated in upflow mode, said reactors being operated in parallel, are employed, and wherein in stage (iii), one adiabatic shaft reactor or two adiabatic shaft reactors being continuously operated in upflow mode, are employed. Still more preferably, the reaction in at least one of these reactors, more preferably in the at least two reactors of stage (i) and still more preferably in all reactors used in states (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS-1 or Ti-MWW catalyst and even more preferably a TS-1 catalyst.

Depending on the specific characteristics of the catalyst which is used as fixed-bed catalyst, it may be necessary to use at least one additional inert compound in order to keep the catalyst, for example the catalyst in the form of shaped bodies such as extrudates or the like, in fixed-bed state. Thus, at least one layer of shaped bodies consisting or essentially consisting of the at least one inert compound can be arranged below or above or below and above a catalyst layer such forming, for example, a sandwich structure. This concept can also be applied to horizontally arranged reactors. In this context, the term "inert compound" relates to a compound which does not participate in the reaction or reactions carried out in the reactor in which the inert compound is employed. As to the present epoxidation reaction, preferred inert compounds are, for example, steatite, high-fired alpha-alumina, carbides, silicides, nitrides, oxides, phosphates, ceramics, non-acidic glasses, suitable metals such as steels of types 1.4306, 1.4307, 1.4541, 1.4571 or comparable materials. Such inert compounds can be used in at least one of the reactors used in (i) and/or (iii).

As to the geometry of the shaped bodies, there are no specific restrictions as long as the catalyst is kept in fixed-bed state. Shaped bodies such as pellets, spheres, cylinders and the like can be employed. Preferred diameters are from 2 to 35 mm, more preferably from 3 to 30 mm and more preferably from 4 to 10 mm.

The hydrogen peroxide is used in the process according to the invention in the form of an aqueous solution with a hydrogen peroxide content of generally of from 1 to 90 wt.-%, preferably of from 10 to 70 wt.-%, more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, 5th edition, volume 3 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one non-acidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all non-acidic ion exchanger beds comprising cation exchangers and/or anion exchangers. It is also possible for cation and anion exchangers to be used as mixed beds within one ion exchanger bed. In a preferred embodiment of the present invention, only one type of non-acidic ion exchangers is used. Further preference is given to the use of basic ion exchange, particularly preferably that of a basic anion exchanger and more particularly preferably that of a weakly basic anion exchanger.

The reaction in the reactors according to stage (i) is preferably carried out at reaction conditions such that the hydrogen peroxide conversion is at least 80%, more preferably at least 85% and still more preferably at least 90%. The pressure in the reactors is generally in the range of from 10 to 30 bar, more preferably from 15 to 25 bar. The temperature of the cooling water is in the range of preferably from 20 to 70° C., more preferably from 25 to 65° C. and particularly preferably from 30 to 60° C.

According to the preferred embodiment of the invention according to which the reactor or the reactors in stage (i) are fixed-bed reactors, the product mixture obtained therefrom essentially consists of propylene oxide, unreacted propene, methanol, water, and unreacted hydrogen peroxide, and optionally propane.

According to stage (ii), unreacted propene is separated from the mixture resulting from stage (i). This separation can be conducted by essentially every suitable method. Preferably, this separation is carried out by distillation using at least one distillation column. The reaction mixture obtained from the at least one reactor, preferably from the at least two reactors used in stage (i), comprising unreacted propene, propylene oxide, methanol, water and unreacted hydrogen peroxide and optionally propane, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

The temperature of the product mixture obtained from stage (i) is preferably in the range of from 40 to 60° C., more preferably of from 45 to 55° C. Prior to being fed to the distillation column of (ii), the product mixture is preferably heated up in at least one heat exchanger to a temperature in the range of from 50 to 80° C., more preferably of from 60 to 70° C.

According to an object of the present invention, heating up the product stream obtained from stage (i) is carried out using, at least partially, the bottoms stream of the distillation column of stage (ii). Thus, heat integration of the overall epoxidation process is improved. According to a preferred embodiment, of from 50 to 100%, more preferably of from 80 to 100% and especially preferably of from 90 to 100% of the bottoms stream obtained from the distillation column used in (ii) are used for heating up the product stream obtained from (i) from a temperature in the range of from 45 to 55° C. to a temperature in the range of from 65 to 70° C.

At the top of the distillation column of (ii), a stream essentially consisting of propylene oxide, methanol, and unreacted propene, is obtained. At the top of the column, a mixture is obtained having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

Therefore, depending on the respective point of view, distillative separation according to stage (ii) can be described as separation of unreacted propene or, alternatively, as separation of propylene oxide.

According to a preferred embodiment of the present invention, the evaporator of the distillation column used in stage (ii) is at least partially operated using at least partially a top stream (Td). Preferably, from 5 to 60%, more preferably from 15 to 50% and especially preferably from 20 to 40% of (Td) are used to operate the evaporator of the distillation column of stage (ii). This top stream (Td) is most preferably obtained in the inventive epoxidation process in a work-up stage where methanol is separated from a mixture comprising water and of methanol as referred hereinunder as stage (c2).

According to a still further preferred embodiment, the distillation column used in (ii) is configured as dividing wall column having at least one side-offtake, preferably one side-offtake. Preferably, the dividing wall column preferably has from 20 to 60, more preferably from 30 to 50 theoretical stages. The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage. In the above mentioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar. The distillation is then preferably carried out in a temperature range from 65 to 100° C., more preferably from 70 to 85° C. The distillation temperature is measured at the bottom of the tower.

In case such a divided wall column is used, at the top of the distillation column of (ii), a stream essentially consisting of propylene oxide, methanol, and unreacted propene, is obtained. At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propene content of from 15 to 35 wt.-%, preferably of from 20 to 30 wt.-% and still more preferably of from 20 to 25 wt.-%, a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream.

At the side-offtake of the distillation column, a stream essentially consisting of methanol and water is obtained. At the side-offtake of the column, a mixture is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (i) of the inventive process. Preferably, at least 90%, more preferably at least 95% of the stream taken from the side-offtake are recycled into stage (i).

Therefore, the present invention relates to a process as described above, wherein at least 90% of the stream taken from the side-offtake of the distillation column used in (ii) are recycled into stage (i).

The bottoms stream taken from the distillation column, preferably the dividing wall distillation column, essentially consisting of methanol, water and unreacted hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh propene is additionally added directly into the reactor of stage (iii) or added to the bottoms stream obtained from (ii) prior to introducing same into the reactor of stage (iii). Alternatively or additionally, fresh hydrogen peroxide can be added.

The selectivity of this reaction in stage (iii) with respect to hydrogen peroxide is preferably in the range from 64 to 99%, more preferably in the range from 72 to 90% and particularly preferably in the range from 75 to 87%.

The selectivity of the overall process in stages (i) to (iii) with respect to hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The reaction mixture obtained from stage (iii) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The propylene oxide content, preferably in the range of from 1 to 5 wt.-%, more preferably of from 1 to 4 wt.-% and especially preferably of from 1 to 3 wt.-%, based on the total weight of the reaction mixture. The propene content is preferably in the range of from 0 to 5 wt.-%, more preferably of from 0 to 3 wt.-% and especially preferably of from 0 to 1 wt.-%, based on the total weight of the reaction mixture.

The product mixture taken from the reactor of stage (iii) can be subjected directly, without any intermediate stage, to the propylene oxide separation of stage (a).

If unreacted propene is present in the mixture taken from the reactor of stage (iii), it may be desirable to at least partially separate propene from this mixture prior to separation of propylene oxide. In this case, at least a portion of the stream taken from the top of the distillation column of stage (ii) can be combined with the product mixture taken from the reactor of stage (iii) to give a mixture which is then fed to propene separation. Alternatively, it is possible to separately feed the product mixture obtained from stage (iii) and at least a portion of the top stream of the distillation column of stage (ii) into propene separation.

Either from the mixture obtained from stage (iii) or from the mixture obtained from propene separation, as described above, propylene oxide is separated in stage (a) of the inventive process. This separation can be conducted by every suitable method. Most preferably, separation is conducted by distillation which is preferably carried out in at least one distillation column, more preferably in one distillation column. Preferably, this column has of from 30 to 110, more preferably of from 40 to 100 and especially preferably of from 50 to 90 theoretical stages. The distillation column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

According to a preferred embodiment of the present invention, the evaporator of the distillation column used for separating propylene oxide in stage (a) is at least partially operated using at least partially a top stream (Td). Preferably from 1 to 50 wt.-% of (Td), more preferably from 1 to 40 wt.-% of (Td) and especially preferably from 2 to 30 wt.-% of (Td) are specifically used to start the operation of the evaporator of the distillation column used for separating propylene oxide, and preferably from 50 to 100% of the compressed top stream of this distillation column, still more preferably from 80 to 95% of this top stream are used to completely operate the evaporator of the distillation column once the distillation column fully operates. Therefore, (Td) is partially used to start the operation of the evaporator, and the compressed top stream obtained from stage (c) takes over operation of the evaporator. This top stream (Td) is most preferably obtained in the inventive epoxidation process in a work-up stage where methanol is separated from a mixture comprising water and of methanol as referred hereinunder as stage (c2).

According to this preferred distillative propylene oxide separation of stage (a), a mixture (Ma) is obtained as bottoms stream comprising water and at least 55 wt.-% of methanol. According to a preferred embodiment of the inventive process, the mixture (Ma) obtained comprises of from 55 to 85 wt.-%, more preferably from 65 to 80 wt.-% and especially preferably from 75 to 79 wt.-% of methanol, and of from 10 to 40 wt.-%, more preferably from 15 to 30 wt.-% and especially preferably of from 15 to 25 wt.-% of water. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

According to an alternative of stage (a), the reaction mixture obtained from stage (iii), alone or optionally in combination with the top stream obtained from separation stage (ii), can be subjected to a first separation stage where propene and propylene oxide are suitably separated together, preferably by distillation in at least one distillation column, to obtain a mixture (Ma) comprising water and at least 55 wt.-% of methanol, and another mixture comprising propene and propylene oxide. Distillation is preferably carried out in at least one distillation column, more preferably in one distillation column. Preferably, this column has of from 30 to 110, more preferably of from 40 to 100 and especially preferably of from 50 to 90 theoretical stages. Distillation is preferably performed at a pressure of from 1 to 20 bar, more preferably from 2 to 10 bar and still more preferably from 3 to 7 bar. From the latter mixture, propylene oxide can be separated. Propene thus obtained can be recirculated as starting material into the epoxidation reaction, preferably into stage (i) and/or stage (iii). Mixture (Ma) thus obtained preferably comprises of from 55 to 85 wt.-%, more preferably from 65 to 80 wt.-% and especially preferably from 75 to 79 wt.-% of methanol, and of from 10 to 40 wt.-%, more preferably from 15 to 30 wt.-% and especially preferably of from 15 to 25 wt.-% of water. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

Additionally, mixture (Ma) obtained from stage (a) after separation of propylene oxide comprises at least one carboxylic acid having from 1 to 3 carbon atoms and at least one carbonyl compound having from 1 to 3 carbon atoms, wherein the carbonyl compound is an aldehyde or a ketone.

Preferably, mixture (Ma) comprises from 0.001 to 0.5 wt.-%, more preferably from 0.01 to 0.5 wt.-% and more preferably from 0.1 to 0.5 wt.-% of the at least one carboxylic acid, wherein the given weight percent ranges refer to the sum of the carboxylic acids having 1 to 3 carbon atoms contained in (Ma). Specific examples are formic acid, acetic acid and propionic acid. Thus, (Ma) may contain formic acid or acetic acid or propionic acid or formic acid and acetic acid or formic acid and propionic acid or acetic acid and propionic acid or formic acid and acetic acid and propionic acid.

Preferably, mixture (Ma) comprises from 0.01 to 0.2 wt.-%, more preferably from 0.03 to 0.15 wt.-% and more preferably from 0.05 to 0.1 wt.-% of the at least one carbonyl compound, wherein the given weight percent ranges refer to the sum of the carbonyl compounds having 1 to 3 carbon atoms contained in (Ma). Specific examples are formaldehyde, acetaldehyde and propionaldehyde. Thus, (Ma) may contain formaldehyde or acetaldehyde or propionaldehyde or formaldehyde and acetaldehyde or formaldehyde and propionaldehyde or acetaldehyde and propionaldehyde or formaldehyde and acetaldehyde and propionaldehyde.

Without wanting to be bound to any theory, it is believed that the at least one carboxylic acid and/or the at least one carbonyl compound can result as by-product from the epoxidation reaction and/or as products from reactions of side products or by-products of the epoxidation reaction, either in the epoxidation reaction itself and/or during work-up of the reaction mixture resulting from the epoxidation reaction, e.g. during separation of unreacted propene in stage (ii) and/or during separation of propene prior to separation of propylene oxide and/or during separation of propylene oxide. Since the process is carried out as integrated process, i.e. at least one compound, namely at least methanol, is separated during work-up and recirculated into the process, the at least one carboxylic acid and/or the at least one carbonyl compound can result from any other work-up step which carried out after step (b) and can be recirculated into the process as contaminants of the recirculated compound, such as methanol.

Stage (b)

According to stage (b) of the inventive process, the at least one carboxylic acid comprised in (Ma) is at least partially neutralized by adding a base to mixture (Ma) to obtain a mixture (Mb).

There are no specific restrictions as to which base or which mixture of bases is used to at least partially neutralize the at least one carboxylic acid. Particularly preferably, the base does not contain a —$NH_2$ group. Bases are preferred which contain alkali metal ions such as lithium, sodium, potassium or cesium or alkaline earth metal ions such as magnesium, calcium or barium. Especially preferred are bases which contain alkali metal ions, more preferably lithium or sodium or potassium or barium or a mixture of two, three or four of these alkali metal ions.

While there are no specific restrictions as to the how these bases are introduced into (Ma), it is preferred to introduce them as an aqueous solution.

Therefore, the present invention also relates to a process as described above, wherein in (b), an aqueous alkaline solution is added as base.

Preferably, the base comprises, as anion, carbonate ions, hydrogen carbonate ions, hydroxyl ions, or a mixture of two or more of these species. Thus, it is preferred to employ alkali or alkaline earth carbonates and/or alkali or alkaline earth hydrogen carbonates and/or alkali or alkaline earth hydroxides or mixtures of two or more thereof. It is further preferred to use hydroxide ions, especially preferably solution comprising hydroxide ions.

Therefore, the present invention also relates to a process as described above, wherein in (b), an aqueous solution comprising hydroxide ions is added as base.

Even more preferably, alkali earth hydroxides and still more preferably sodium hydroxide. In each case, it is especially preferred to employ the respective alkali or alkaline earth compound as aqueous solution.

Therefore, the present invention also relates to a process as described above, wherein in (b), an aqueous alkaline solution comprising hydroxide ions is added as base.

While it is possible to carry out stage (b) of the inventive process in the presence of a decomposition catalyst, it is particularly preferred to add the base in the absence of a decomposition catalyst, especially in the absence of a decomposition catalyst comprising a group VIII metal or an oxide thereof.

The concentration of the aqueous solution employed in stage (b) based on hydroxide ions is preferably in the range of from 0.25 to 25 mol/l, more preferably from 1 to 17 mol/l and still more preferably from 6 to 11 mol/l.

According to stage (b), the at least one carboxylic acid is at least partially neutralized. Therefore, it is preferred to introduce the aqueous solution comprising hydroxide ions in an amount such that the molar ratio of hydroxide ions introduced in (b) relative to carboxylic acid comprised in (Ma) is from 0.1 to 10, more preferably from 0.5 to 5 and still more preferably from 1 to 2.

Therefore, the present invention also relates to a process as described above, wherein the molar ratio of hydroxide ions introduced in (b) relative to carboxylic acid comprised in (Ma) is from 0.1 to 10.

Adding of the base according to stage (b) of the process can be carried out in a suitable separate vessel or reactor in continuous and/or discontinuous manner. It is also possible to add the base to the stream which is fed into stage (c) by simply feeding the base and the stream through a static mixer into stage (c). Moreover, it is possible to fed the stream to be treated with base to the at least one distillation column used in stage (c) and suitably introduce the base as separate feed into this distillation column. Also a combination of these methods is possible so that, e.g., a portion of the base is fed as separated stream into the at least one distillation column of stage (c) and another portion of the base is fed together with the stream through a static mixer into stage (c).

Preferably, the pH of the stream to which the base has had been added and which is to be separated by distillation according to stage (c), is in the range of from greater than 7 and less than 10, more preferably of from 8 to 9.

Stage (c)

According to stage (c) of present invention, methanol is separated by distillation from mixture (Mb) which results from adding the base to mixture (Ma). More preferably, methanol is separated from water. Still more preferably, methanol is additionally separated from at least one compound having a boiling temperature lower than methanol and lower than water at a given pressure by distillation in stage (c). Specific examples of such compounds are carbonyl compounds having from 1 to 3 carbon atoms contained in (Ma) such as formaldehyde, acetaldehyde or propionaldehyde, including aceotropes of these compounds with methanol or with water or with methanol and water. Other examples of such compounds are acetal compounds such as formaldehyde dimethylacetal, acetaldehyde dimethylacetal, propionaldehyde dimethylacetal or 4-methyl-1,3-dioxolane including aceotropes of these compounds with methanol or with water or with methanol and water.

Without wanting to be bound to any theory, it is believed that these acetal compounds are formed as primary, secondary or higher by-products of the epoxdiation reaction during stage (a) and/or are formed during one or more work-up stages prior to stage (c) and/or are formed during one or more work-up stages after stage (c) and recirculated into the process together with methanol recirculated into stage (a) according to stage (d).

Separating of methanol by distillation can be performed in one, two, three, four or more distillation columns. While it is principally possible to separate methanol in one column, it is preferred to employ at least two columns such as two, three, or four columns.

According to a first alternative, methanol is separated from mixture (Mb) which contains at least one compound having a boiling temperature lower than methanol and lower than water at a given pressure, by distillation using one distillation column.

According to a second alternative, the at least one compound having a boiling point lower than methanol and water is separated from mixture (Mb) in a stage (c1). Then, water is separated from methanol in a stage (c2). While there are no specific restrictions as the respective separation methods, distillative separation is preferred.

Preferably, according to the second alternative, methanol is separated from mixture (Mb) which contains at least one compound having a boiling temperature lower than methanol and lower than water at a given pressure, by (c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises at least 5 wt.-% of the at least one compound having a boiling point lower than methanol and water;

(c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 90 wt.-% of water.

In this case, distillation according to (c1) is preferably performed at a pressure of from 0.5 to 5 bar, more preferably from 0.5 to 2 bar and still more preferably from 0.8 to 1.5 bar, the distillation column used preferably having from 10 to 60, more preferably from 15 to 40 theoretical plates.

Distillation according to (c2) is preferably performed at a pressure of from 1 to 15 bar, more preferably from 3 to 14 bar and still more preferably from 5 to 12 bar, the distillation column used preferably having from 5 to 80, more preferably from 10 to 60 and still more preferably from 20 to 50 theoretical plates. The mixture (Mc2i) obtained at the top of the column is referred to hereinabove as top stream (Td).

Preferably, mixture (Mb1) obtained according to the second alternative comprises from 40 to 85 wt.-%, more preferably from 60 to 80 wt.-% of methanol, preferably from 10 to 55 wt.-%, more preferably from 15 to 30 wt.-% of water and preferably at most 0.1 wt.-%, more preferably at most 0.01 wt.-% of the at least one compound having a boiling point lower than methanol and water.

Preferably, mixture (Mc2i) obtained according to the second alternative comprises from 85 to 99.5 wt.-%, more preferably from 90 to 99 wt.-% of methanol, preferably from 0.1 to 10 wt.-%, more preferably from 0.5 to 5 wt.-% of water and preferably less than 150 ppm, more preferably less than 100 ppm of the at least one compound having a boiling point lower than methanol and water.

Mixture (Mb2) obtained according to the second alternative which contains essentially the complete amount of the at least one compound having a boiling point lower than methanol and water which had been contained in mixture (Mb) can be at least partially subjected to one or more suitable separation stages and/or be at least partially fed to at least one energy recovery unit.

Distillative separation in (c1) and/or (c2) can be also performed in two, three or more columns wherein the pressures under which distillation is carried out in each column used in (c1) and/or (c2) can be the same or different.

According to a third alternative, the at least one compound having a boiling point lower than methanol and water is separated from mixture (Mb) together with methanol in a stage (c1). Then, methanol is separated from the at least one compound having a boiling point lower than methanol and water in a stage (c2). While there are no specific restrictions as the respective separation methods, distillative separation is preferred.

Preferably, according to the third alternative, methanol is separated from mixture (Mb) which contains at least one compound having a boiling temperature lower than methanol and lower than water at a given pressure, by (c1) separating water from mixture (Mb) by distillation to obtain a mixture (Mb1) and a mixture (Mb2), wherein mixture (Mb1) comprises at least 85 wt.-% of methanol, up to 10 wt.-% of water and at most 5 wt.-% of the at least one compound having a boiling point lower than methanol and water, and wherein mixture (Mb2) comprises at least 90 wt.-% of water and at most 0.1 wt.-% of the at least one compound having a boiling point lower than methanol and water and at most wt.-% of methanol (c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 5 wt.-% of the at least one compound having a boiling point lower than methanol and water.

In this case, distillation according to (c1) is preferably performed at a pressure of from 1 to 15 bar, more preferably from 3 to 14 bar and still more preferably from 5 to 12 bar, the distillation column used preferably having from 10 to 60, more preferably from 20 to 50 theoretical plates.

Distillation according to (c2) is preferably performed at a pressure of from 0.5 to 5 bar, more preferably from 0.6 to 2 bar and still more preferably from 0.8 to 1.5 bar, the distillation column used preferably having from 10 to 60, more preferably from 15 to 40 and still more preferably from 15 to 30 theoretical plates.

Preferably, mixture (Mb1) obtained according to the third alternative comprises from 85 to 99.5 wt.-%, more preferably from 90 to 99.5 wt.-% of methanol, preferably from 0.1 to 10 wt.-%, more preferably from 0.5 to 5 wt.-% of water and preferably from 0.005 to 1 wt.-%, more preferably from 0.01 to 0.5 wt.-% of the at least one compound having a boiling point lower than methanol and water.

Preferably, mixture (Mc2i) obtained according to the third alternative comprises from 85 to 99.5 wt.-%, more preferably from 90 to 99 wt.-% of methanol, preferably from 0.1 to 10 wt.-%, more preferably from 0.5 to 5 wt.-% of water and preferably less than 150 ppm, more preferably less than 100 ppm of the at least one compound having a boiling point lower than methanol and water.

Mixture (Mb2) obtained according to the third alternative which contains essentially the complete amount of the at least one compound having a boiling point lower than methanol and water which had been contained in mixture (Mb) can be at least partially subjected to one or more suitable separation stages and/or be at least partially fed to at least one energy recovery unit.

Distillative separation in (c1) and/or (c2) can be also performed in two, three or more columns wherein the pressures under which distillation is carried out in each column used in (c1) and/or (c2) can be the same or different.

Stage (d)

From stage (c), a methanol stream is obtained which results from separation of water and the at least one compound having a boiling point lower than methanol and water. According to the present invention, this methanol stream has a content with regard to carbonyl compounds which is 200 ppm or less. Preferably, mixtures (Mc2i) comprise 150 ppm or less, still more preferably 100 ppm or less such as from 10 to 100 ppm of these at least one compound having a boiling point lower than methanol and water. More preferably, mixtures (Mc2i) comprise at least 90 wt.-%, more preferably 95 wt.-% of methanol and still more preferably at least 97 wt.-% of methanol. Mixture (Mc2i) is then recirculated as solvent into stage (a) of the process, preferably as solvent into stage (i) and/or stage (iii) where propene is epoxidized with hydrogen peroxide.

While not wanting to be bound to any theory, it is believed that adding the base in stage (b) leads to at least partial neutralisation of the carboxylic acids, which neutralisation in turn prevents at least partially the formation of acetal compounds and/or ester compounds, such as formaldehyde dimethylacetal, acetaldehyde dimethylacetal, propionaldehyde dimethylacetal or 4-methyl-1,3-dioxolane, in the work-up stages of methanol and thus prevents the concentration of these acetal compounds from having too high a value in the methanol stream which is recirculated into stage (a). Additionally, it is believed that this allows for an easily to be accomplished separation of the at least one compound having a boiling point lower that methanol and lower than water such as carbonyl compounds having from 1 to 3 carbon atoms like formaldehyde, acetaldehyde, propionaldehyde, especially preferably acetaldehyde.

Mixture (Ma) which is obtained from stage (a) of the process of the present invention can additionally comprise other primary and/or secondary and/or higher by-products of the epoxidation process. Specifically, compounds comprising at least one hydroperoxy group, i.e. a —O—O—H group, are to be mentioned. More specifically, compounds are to be mentioned which contain at least one hydroxy group and at least one hydroperoxy group wherein the term "hydroxy group" refers to a hydroxy group which is not a portion of the hydroperoxy group. Most preferably, mixture (Ma) obtained from stage (a) comprises 2-hydroperoxypropanol-1,1-hydroperoxypropanol-2 or a mixture of 2-hydroperoxy-propanol-1 and 1-hydroperoxypropanol-2.

According to an especially preferred embodiment of the present invention, a mixture (Ma) obtained form stage (a), comprising a compound which contains at least one hydroperoxy group, more preferably at least one hydroperoxy group and at least one hydroxy group, and still more preferably 2-hydroperoxypropanol-1,1-hydroperoxypropanol-2 or a mixture of 2-hydroperoxy-propanol-1 and 1-hydroperoxypropanol-2, is subjected to a suitable reduction stage prior to stage (b) of the inventive process where the compounds comprising at least one hydroperoxy group are reduced to give the respective alcohol compound, e.g. propanediol.

Another compound which can be contained in mixture (Ma) and which can be subjected to reduction to give the respective alcohol compound is hydroxy acetone, $H_3C$—CO—$CH_2OH$. It is believed that hydroxy acetone is a primary and/or secondary and/or higher by-product of the epoxidation process or a subsequent work-up stage. Preferably, hydroxy acetone is reduced to give propanediol.

Among others, as suitable reducing agents, phosphorus (III) compounds such as $PCl_3$, phosphines (e.g. triphenylphosphine, tributylphosphine), phosphorous acid or its salts or sodium hypophosphite ($NaH_2PO_2$), sulfur(II) compounds, for example $H_2S$ or its salts, sodium polysulfides ($Na_2S_x$, x>1), dimethyl sulfide, tetrahydrothiophene, bis(hydroxyethyl) sulfide or sodium thiosulfate ($Na_2S_2O_3$), or sulfur(IV) compounds, for example sulfurous acid ($H_2SO_3$) and its salts, sodium bisulfite ($Na_2S_2O_5$) or thiourea S-oxide, or nitrites, for example sodium nitrite or isoamyl nitrite, or α-hydroxycarbonyl compounds, for example hydroxyacetone, dihydroxyacetone, 2-hydroxycyclopentanone (glutaroin), 2-hydroxycyclohexanone (adipoin), glucose and other reducible sugars, or enediols, for example ascorbic acid, or compounds which contain a B—H bond, for example sodium borohydride or sodium cyanoborohydride, are to be mentioned. According to preferred embodiments of the present invention, reducing agents used for the reduction stage do not contain sulfurous acid, sodium hydrogen sulfite, sodium sulfite, sodium metabisulfite, sodium borohydride, potassium borohydride and suitable combinations or mixtures thereof.

In the process of the present invention, particular preference is given to reduce mixture (Ma) obtained from stage (a) by catalytic hydrogenation using a suitable compound enabling hydrogenation of mixture (Ma), i.e. the at least compound comprising at least one hydroperoxy group contained in (Ma). An example of such a suitable compound is hydrogen in the presence of a suitable hydrogenation catalyst.

Preferably, for the purposes of the present invention, catalytic hydrogenation is thus the reaction of an hydroperoxyalcohol-containing product, mixture with hydrogen in the presence of a suitable hydrogenation catalyst.

Thus, the present invention also provides a process as described above, wherein prior to (b), mixture (Ma) is subjected to catalytic hydrogenation.

The hydrogenation catalyst in question can be either homogeneous or heterogeneous. For the purposes of the present invention, the catalytic hydrogenation is preferably carried out in the presence of a heterogeneous catalyst.

The hydrogenation catalyst comprises at least one active metal of group VIIb, VIII, Ia or Ib of the Periodic Table of the Elements, either individually or as a mixture of two or more thereof.

In the process of the present invention, use is made of palladium (Pd), platinum (Pt), rhodium (Rh), ruthenium (Ru), iridium (Ir), osmium (Os), iron (Fe), cobalt (Co), nickel (Ni) and copper (Cu), preferably Pd, Pt, Rh, Ru and Ir. According to especially preferred embodiments of the present invention, Ru is not used as active metal. Even more preferred is the use of Pd. In case Pd is used as active material, the catalyst can additionally contain Ag.

Therefore, the present invention also provides a process as described above, wherein the hydrogenation catalyst employed for catalytic hydrogenation comprises a catalytically active metal selected from the group consisting of Pd, Pt, Rh, Ir, Os and a mixture of two or more thereof, more preferably a process as described above, wherein the hydrogenation catalyst employed essentially consists of Pd with regard to the catalytically active metal.

The catalytically active metals can be used in powder form. The active metal powder can be prepared by various methods. Customary methods are, for example, thermal decomposition of active metal salts, the reduction of aqueous or non-aqueous active metal salt solutions using, for example, hydrazine, formaldehyde, hydrogen or other reducing agents. Active metal powders can comprise one active metal or a mixture of two or more thereof.

Active metal bodies can also be used for the hydrogenation. In this case, foils, wires, meshes (which can be prepared by weaving and knitting), granules and crystallite powders produced from one active metal or a mixture of two or more thereof are preferably employed.

Furthermore, it is also possible to use active metal oxides, for example as suspensions comprising one active metal or a mixture of two or more thereof, for the catalytic hydrogenation.

In the process of the present invention, preference is given to using hydrogenation catalysts which comprise a composite of an active metal or a mixture of two or more thereof and at least one support material.

The active metal content is, if the active metal is selected from the group consisting of Pd, Pt, Rh, Ir and Os, generally in a range from 0.01 to 10% by weight. If an active metal selected from the group consisting of Fe, Co, Ni and Cu is present, the content is generally in a range from 1 to 80% by weight.

Support materials which can be used are all materials which are known for this purpose to those skilled in the art and have sufficient chemical and thermal stability for the respective use. Examples are porous oxides such as aluminum oxide, silicon dioxide, aluminosilicates, zeolites, titanium oxide, zirconium oxide, chromium oxide, zinc oxide, magnesium oxide, rare earth oxides, and also activated carbon or mixtures of two or more of the compounds mentioned. Furthermore, all types of support materials described in EP 0 827 944 A1 can also be used.

The composites which can be produced from an active metal or a mixture of two or more thereof and at least one support, known as supported catalysts, can be produced by any method known to those skilled in the art.

For example, such supported catalysts are generally obtainable by impregnating the support or supports with a solution of the active metal or mixture of two or more thereof; in the case of a plurality of active metals, these can be added simultaneously or in succession. It is possible to impregnate the support fully or only partly with such a solution.

Of course, it is also possible to spray the respective solution of appropriate active metals onto the support by methods known per se or to apply the active metals to the support by vapor deposition or by electrochemical deposition. The application of the active metal or a mixture of two or more thereof can also be carried out in the manner described in EP 0 827 944 A1.

In both methods, the desired alkali metal loading of the support is set via the concentration of the active metal solution selected in each case.

In the catalyst precursors produced in this way, the active metal or mixture of two or more thereof can be uniformly distributed over the radius or can be present in higher concentration in a shell. In the present case, a shell is an outer radial region of the catalyst precursor (support) in which the active metal is present in a higher concentration than in the other regions of the catalyst precursor (support).

Impregnation or spraying can generally be followed by further steps such as a drying step and/or a heat treatment and also a calcination step.

Supported catalysts can generally also be obtained by precipitating at least one pre-cursor of the active metal in the presence of at least one suitable support material by means of alkali or a reducing agent. The catalyst precursors obtained in this way can then be brought into a shape suitable for the respective application, for example extrudates or pressed pellets. This can generally also be followed by the abovementioned further steps such as drying, heat treatment and calcination.

As precursors of the active metals, it is in principle possible to use all water-soluble active metal compounds, for example readily water-soluble salts or complexes of the active metals, e.g. nitrates, nitrosyl nitrates, chlorides, acetates, formates and sulfates and also chlorometalates.

Drying of the catalyst precursors can be carried out by all drying methods known to those skilled in the art. For the purposes of the present invention, the drying process is preferably carried out at from 80 to 150° C., particularly preferably from 80 to 120° C.

The calcination of the catalyst precursors can be carried out in any way known to those skilled in the art. For the purposes of the present invention, the catalyst precursors obtained are preferably exposed to a gas stream comprising air or nitrogen at from 150 to 500° C., particularly preferably from 200 to 450° C.

In general, the calcination process can be followed by the activation of the catalyst pre-cursors obtained in this way.

Activation can be carried out by all methods known for this purpose to those skilled in the art in which the catalyst precursors are exposed to a reducing atmosphere, for example a hydrogen-containing atmosphere at room temperature or elevated temperature.

For the purposes of the present invention, preferred catalyst precursors comprising an active metal selected from the group consisting of Pd, Pt, Rh, Ir and Os can be treated with hydrogen at from 80 to 250° C., preferably from 80 to 180° C. Catalyst precursors comprising an active metal selected from the group consisting of Fe, Co, Ni and Cu are preferably treated with hydrogen at from 150 to 500° C., particularly preferably from 200 to 450° C.

The duration of the treatment with hydrogen at room temperature or elevated temperatures depends on the concentration of the active metal or mixture of two or more thereof.

For the purposes of the present invention, the duration of the treatment is preferably from 0.5 to 24 hours, particularly preferably from 1 to 5 hours, in the preferred case of catalyst precursors comprising an active metal selected from the group consisting of Pd, Pt, Rh, Ir and Os. In the case of catalyst precursors comprising an active metal selected from the group consisting of Fe, Co, Ni and Cu, the duration of the treatment is preferably from 12 to 120 hours, particularly preferably from 24 to 72 hours.

The space velocity of hydrogen in the activation carried out for the purposes of the present invention is generally from 1 to 100 $l\,kg^{-1}_{catalyst}\,h^{-1}$, but preferably from 10 to 50 $l\,kg^{-1}_{catalyst}h^{-1}$.

The hydrogenation catalysts prepared in the above-described way make it possible to carry out hydrogenations by any method known to those skilled in the art, for example in the liquid phase, in a fixed bed or in suspension and in the upflow mode or downflow mode. However, the hydrogenation in the process of the present invention is preferably carried out in a fixed bed.

Depending on the specific characteristics of the catalyst which is used as fixed-bed catalyst, it may be necessary to use at least one additional inert compound in order to keep the catalyst, for example the catalyst in the form of shaped bodies such as extrudates or the like, in fixed-bed state. Thus, at least one layer of shaped bodies consisting or essentially consisting of the at least one inert compound can be arranged below or above or below and above a catalyst layer such forming, for example, a sandwich structure. This concept can also be applied to horizontally arranged reactors. In this context, the term "inert compound" relates to a compound which does not participate in the reaction or reactions carried out in the reactor in which the inert compound is employed. As to the present epoxidation reaction, preferred inert compounds are, for example, steatite, high-fired alpha-alumina, carbides, silicides, nitrides, oxides, phosphates, ceramics, non-acidic glasses, suitable metals such as steels of types 1.4306, 1.4307, 1.4541, 1.4571 or comparable materials. Such inert compounds can be used in at least one of the reactors used in (i) and/or (iii).

Pressure and temperature ranges in the hydrogenation are chosen as a function of the substance or mixture to be hydrogenated. In the process of the present invention, the hydrogenation is preferably carried out in a pressure range from 1 to 100 $bar_{abs}$, particularly preferably from 1 to 10 $bar_{abs}$, and preferably at temperatures in the range from 0 to 180° C., more preferably from 25 to 120° C., in particular from 65 to 85° C.

The hydrogen partial pressure during hydrogenation is preferably in the range of from more than 1 to 25 bar, preferably from more than 1 to 20 bar, such as from 2 to 20 bar or preferably from 3 to 20 bar, and more preferably from 2 to 15 bar and still more preferably from 3 to 13 bar.

Therefore, the present invention also provides a process as described above, wherein catalytic hydrogenation is carried out at a temperature of from 65 to 85° C. and at a hydrogen partial pressure of from 3 to 20 bar.

Therefore, the present invention also provides a process as described above, wherein catalytic hydrogenation is carried out at a temperature of from 65 to 85° C. and at a hydrogen partial pressure of from 3 to 13 bar.

In a hydrogenation carried out in a fixed bed, the residence time of the liquid is from 1 second (s) to 1 hour (h), preferably from 10 s to 20 minutes (min), in particular from 30 s to 5 min.

Accordingly, the catalyst used in the catalytic hydrogenation of an α-hydroperoxyalcohol-containing product mixture formed in the epoxidation according to the present invention is selected from the group consisting of heterogeneous catalysts comprising Ru, Ni, Pd, Pt, either individually or as a mixture of two or more thereof, as active metal on a suitable support material.

Preference is given to using supported catalysts which are produced by one of the above-described methods and are used for the hydrogenation of the hydroperoxyalcohol-containing mixture (Ma), more preferably for the hydrogenation of mixture (Ma) comprising 2-hydroperoxypropanol-1,1-hydroperoxypropanol-2 or a mixture of 2-hydroperoxy-propanol-1 and 1-hydroperoxypropanol-2. Additionally or alternatively, (Ma) can contain hydroxy acetone.

Thus, the present invention also provides a process as described above wherein the mixture (Ma) additionally comprises 2-hydroperoxypropanol-1,1-hydroperoxypropanol-2 or a mixture of 2-hydroperoxy-propanol-1 and 1-hydroperoxypropanol-2 and/or hydroxy acetone, and wherein prior to (b), the mixture (Ma) is subjected to a catalytic hydrogenation to give a mixture comprising 1,2-dihydroxypropane.

The mixture which is obtained from stage (a) and which is then subjected to catalytic hydrogenation is subsequently subjected to stages (b) of the process of the present invention. Thus, according to preferred embodiments of the inventive process, mixtures comprising 1,2-dihydroxypropane are fed to separation stage (c).

According to a first alternative of the inventive process described above, according to which methanol is separated from mixture (Mb) which contains at least one compound having a boiling temperature lower than methanol and lower than water at a given pressure, by distillation using one distillation column, 1,2-dihydroxypropane is separated together with methanol from mixture (Mb). The resulting mixture which is essentially free of the at least one compound having a boiling temperature lower than methanol and lower than water can be subjected to further purification stages wherein, e.g., methanol is separated from the at least one compound having a boiling temperature lower than methanol and lower than water.

According to a second alternative of the inventive process described above, according to which methanol is separated from mixture (Mb) which contains at least one compound having a boiling temperature lower than methanol and lower than water at a given pressure, by
(c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises at least 5 wt.-% of the at least one compound having a boiling point lower than methanol and water;
(c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 90 wt.-% of water, 1,2-dihydroxypropane which is additionally contained in (Mb), is separated together with methanol and water and is essentially completely contained in (Mb1). After stage (c2), 1,2-dihydroxypropane is essentially completely contained in mixture (Mc2ii). Preferably, mixture (Mc2ii) comprises from 0.1 to 5 wt.-%, more preferably from 0.5 to 2 wt.-% of 1,2-dihydroxypropane.

According to a third alternative of the inventive process described above, according to which methanol is separated from mixture (Mb) which contains at least one compound having a boiling temperature lower than methanol and lower than water at a given pressure, by
(c1) separating water from mixture (Mb) by distillation to obtain a mixture (Mb1) and a mixture (Mb2), wherein mixture (Mb1) comprises at least 85 wt.-% of methanol, up to 10 wt.-% of water and at least 5 wt.-% of the at least one compound having a boiling point lower than methanol and water, and wherein mixture (Mb2) comprises at least 90 wt.-% of water and at most 0.1 wt.-% of the at least one compound having a boiling point lower than methanol and water and at most wt.-% of methanol
(c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 5 wt.-% of the at least one compound having a boiling point lower than methanol and water, 1,2-dihydroxypropane which is additionally contained in (Mb), is separated together with water in stage (c1) and is essentially completely contained in (Mb2). Preferably, mixture (Mb2) comprises from 0.1 to 5 wt.-%, more preferably from 0.5 to 3 wt.-% of 1,2-dihydroxypropane.

According to even more preferred embodiments, 1,2-dihydroxypropane is additionally separated from mixtures (Mb2) or (Mc2ii) and is obtained as valuable product for further use. Therefore, according a preferred embodiment, the present invention also relates to a process as described above wherein in (c), methanol is separated from mixture (Mb) which contains at least one compound having a boiling temperature lower than methanol and lower than water at a given pressure, by
(c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises at least 5 wt.-% of the at least one compound having a boiling point lower than methanol and water;
(c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 90 wt.-% of water and 1,2-dihydroxypropane, said process further comprising
(e) separating 1,2-dihydroxypropane from mixture (Mc2ii).

Separation according to stage (e) of the inventive process can be carried out by any suitably method, for example by distillation, extraction or membrane permeation. The glycols which have been separated off have a variety of uses. For example, they can be used as starting materials for syntheses in the plastics industry or for the synthesis of naturally occurring compounds and also generally as solvents in large areas of industry. The present invention therefore also provides for the use of the glycols separated off as further useful products in the process of the present invention for further applications in all fields known to those skilled in the art.

In case the catalyst used for hydrogenation according to the present invention is deactivated, it can be replaced by freshly prepared catalyst. Preferably, the deactivated catalyst is at least partially suitably regenerated. If hydrogenation is carried out continuously, which is preferred, the reaction can be stopped in the reactor once the catalyst is deactivated and without or essentially without interruption continued in at least one parallel reactor or by-passed for a short period of time. If the catalyst is used in suspension mode, the deactivated catalyst is suitably separated and suitably externally regenerated. If the catalyst is used in fixed-bed mode, it can be suitably separated and suitably externally regenerated. Preferably, a deactivated catalyst which is used in fixed-bed mode is regenerated in the reactor where the hydrogenation reaction was carried out.

Therefore, according to still another aspect of the present invention, a method is provided which allows for regeneration of the catalyst used for catalytic hydrogenation as described above. Such regeneration is preferably carried out if the catalyst is deactivated to an undesired extent, i.e. if it exhibits 90% or less, preferably 80% or less or more preferably 70% or less of its original performance. The term "regeneration" as used in the context of the present invention relates too a process which allows for improving the catalyst performance compared to the catalyst in its deactivated state.

According to a first embodiment, the deactivated hydrogenation catalyst is regenerated by treatment with at least one suitable solvent. Treatment with solvent is suitably carried out at ambient or higher temperatures, preferably at a temperature of from 60 to 250° C., more preferably of from 80 to 200° C. Thus, the present invention provides a process as described above, wherein the catalyst employed for catalytic hydrogenation is at least partially regenerated by treatment with at least one suitable solvent.

According to even more preferred embodiments, the solvent used for regeneration purposes is selected from solvents used in the present epoxidation process as starting materials, solvents, products or by-products. Among others, hydrogen peroxide solutions, e.g. aqueous hydrogen peroxide solutions, optionally containing, e.g. methanol, or methanol, e.g. as aqueous methanolic solution, propylene oxide, e.g. as aqueous propylene oxide solution, optionally additionally containing methanol, propylene glycol, e.g. 1,2-dihydroxypropane, optionally additionally containing methanol and/or water, methoxypropanol, or mixtures of two or more of these compounds and/or solutions are to be mentioned by way of example.

Therefore, preferred mixtures which can be employed as suitable solvents for regeneration of the hydrogenation catalysts are, e.g., mixtures obtained from stages (c) and (d) and/or (e) of the present process, such as mixtures (Mb1), (Mb2), (Mc2i) and/or (Mc2ii).

Therefore, the present invention also relates to a process as described above wherein the at least one solvent suitable for regeneration of the hydrogenation catalyst is selected from the group consisting of hydrogen peroxide, methanol, water, propylene oxide, propylene glycol, methoxy propanol and mixtures of two or more of these compounds.

According to a second embodiment, the deactivated hydrogenation catalyst is regenerated by treatment at elevated temperature compared to room ambient temperature in the presence of a gas comprising oxygen. Preferably, prior to this treatment, the deactivated catalyst is dried at a temperature lower than the temperature of the treatment for regeneration.

Preferably, the deactivated catalyst is dried at a temperature of from ambient temperature to 200° C., more preferably of from 30 to 150° C. and more preferably of from 50 to 120° C., for a time of preferably from 1 to 48 h, more preferably from 6 to 24 h. Drying is preferably carried out under an atmosphere preferably comprising from 1 to 10 vol.-%, more preferably from 2 to 8 vol.-% of oxygen.

Preferably, the dried catalyst is then treated at a temperature of from ambient temperature to 400° C., more preferably of from 100 to 350° C. and more preferably of from 250 to 350° C., for a time of preferably from 1 to 12 h, more preferably from 2 to 8 h. The atmosphere under which this treatment is carried out preferably comprises from 1 to 10 vol.-%, more preferably from 2 to 8 vol.-% of oxygen.

After treatment, the catalyst is suitably cooled to ambient temperature and re-used in the process of the present invention.

In the context of the present invention, it is also possible to combine both regeneration embodiments, i.e. to treat the deactivated catalyst with at least one suitable solvent and subsequently treat the thus treated catalyst at elevated temperature. It is also possible to treat the deactivated catalyst at elevated temperature and subsequently treat the thus treated catalyst with at least one suitable solvent.

As to the regeneration methods described above, regeneration can be carried out in the apparatus in which hydrogenation is carried out. It is also possible to first suitably remove the catalyst from the apparatus and regenerate it in a separate suitable apparatus.

In the following, preferred processes of the present invention are listed resulting from the following embodiments 1 to 19 including the combinations of these embodiments as explicitly given:

1. A process for the epoxidation of propene, comprising
   (a) reacting propene with hydrogen peroxide in the presence of methanol as solvent and a titanium zeolite catalyst and separating propylene oxide from the resulting reaction mixture to obtain a mixture (Ma) comprising methanol, water, at least one carboxylic acid having from 1 to 3 carbon atoms and at least one carbonyl compound having from 1 to 3 carbon atoms, wherein the carbonyl compound is an aldehyde or a ketone;
   (b) at least partially neutralizing the at least one carboxylic acid comprised in mixture (Ma) by adding a base to mixture (Ma) to obtain a mixture (Mb);
   (c) separating methanol from mixture (Mb) by distillation;
   (d) at least partially recycling the methanol obtained from (c) into (a).
2. The process of embodiment 1, wherein mixture (Ma) comprises from 55 to 85 wt.-% methanol, from 10 to 40 wt.-% water, from 0.001 to 0.5 wt.-% of the at least one carboxylic acid and from 0.01 to 0.2 wt.-% of the at least one carbonyl compound.
3. The process of embodiment 1 or 2, wherein in (b), an aqueous alkaline solution comprising hydroxide ions is added as base.
4. The process of embodiment 3, wherein the molar ratio of hydroxide ions introduced in (b) relative to carboxylic acid comprised in (Ma) is from 0.1 to 10.
5. The process of any of embodiments 1 to 4, wherein in (c), methanol is separated from mixture (Mb) which contains at least one compound having a boiling temperature lower than methanol and lower than water at a given pressure, by
   (c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises at least 5 wt.-% of the at least one compound having a boiling point lower than methanol;
   (c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 90 wt.-% of water.
6. The process of embodiment 5, wherein the at least one compound having a boiling point lower than methanol is selected from the group consisting of formaldehyde, acetaldehyde, propionaldehyde, methyl formate, formaldehyde dimethyl acetal, acetaldehyde dimethyl acetal, and a mixture of two or more thereof.
7. The process of embodiment 5 or 6, wherein in (c1), distillation is carried out at a pressure of from 0.5 to 5 bar.
8. The process of any of embodiments 1 to 7, wherein mixture (Ma) additionally comprises at least one compound comprising a hydroperoxy group and a hydroxy group, where said hydroxy group is not a portion of said hydroperoxy group.
9. The process of any of embodiments 1 to 8, wherein prior to (b), mixture (Ma) is subjected to catalytic hydrogenation.
10. The process of embodiment 9, wherein the hydrogenation catalyst employed for catalytic hydrogenation comprises a catalytically active metal selected from the group consisting of Pd, Pt, Rh, Ir, Os and a mixture of two or more thereof.
11. The process of embodiment 9 or 10, wherein catalytic hydrogenation is carried out at a temperature of from 65 to 85° C. and at a hydrogen partial pressure of from 3 to 20 bar, preferably of from 3 to 13 bar.
12. The process of any of embodiments 1 to 11, wherein the mixture (Ma) additionally comprises 2-hydroperoxypropanol-1,1-hydroperoxypropanol-2 or a mixture of 2-hydroperoxy-propanol-1 and 1-hydroperoxypropanol-2, and wherein prior to (b), the mixture (Ma) is subjected to a catalytic hydrogenation to give a mixture comprising 1,2-dihydroxypropane.
13. The process of embodiment 12, wherein in (c), methanol is separated from mixture (Mb) which contains at least one compound having a boiling temperature lower than methanol and lower than water at a given pressure, by (c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises at least 5 wt.-% of the at least one compound having a boiling point lower than methanol and water;

(c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising at least 90 wt.-% of water and 1,2-dihydroxypropane, said process further comprising (e) separating 1,2-dihydroxypropane from mixture (Mc2ii).

14. The process of any of embodiments 1 to 13, wherein the methanol which is recycled into (a) comprises not more than 200 ppm of carbonyl compounds.

15. The process of any of embodiments 9 to 14, wherein the catalyst employed for catalytic hydrogenation is at least partially regenerated by treatment with at least one suitable solvent.

16. The process of embodiment 15, wherein the at least one suitable solvent is selected from the group consisting of hydrogen peroxide, methanol, water, propylene oxide, propylene glycol and methoxy propanol.

17. The process of any of embodiments 9 to 16, wherein the catalyst employed for catalytic hydrogenation is at least partially regenerated by treatment at elevated temperature in the presence of a gas comprising oxygen.

18. A process for the epoxidation of propene, comprising
(a) reacting propene with hydrogen peroxide in the presence of methanol as solvent and a titanium zeolite catalyst and separating propylene oxide from the resulting reaction mixture to obtain a mixture (Ma) comprising from 55 to 85 wt.-% methanol, from 10 to 40 wt.-% water, from 0.001 to 0.5 wt.-% of at least one carboxylic acid having from 1 to 3 carbon atoms and from wherein the at least one carboxylic acid is selected from the group consisting of formic acid, acetic acid, propionic acid, and a mixture of two or more thereof, and wherein the at least one carbonyl compound is selected from the group consisting of formaldehyde, acetaldehyde, propionaldehyde, and a mixture of two or more thereof;
said mixture (Ma) further comprising from 0.1 to 1 wt.-% of 2-hydroperoxypropanol-1,1-hydroperoxypropanol-2 or a mixture of 2-hydroperoxy-propanol-1 and 1-hydroperoxypropanol-2; and
subjecting mixture (Ma) to catalytic hydrogenation at a temperature of from 65 to 85° C. and at a hydrogen partial pressure of from 3 to 20 bar, preferably of from 3 to 13 bar, to give a mixture comprising from 0.1 to 1.3 wt.-% 1,2-dihydroxypropane, the hydrogenation catalyst comprising a catalytically active metal selected from the group consisting of Pd, Pt, Rh, Ir, Os and a mixture of two or more thereof;
(b) at least partially neutralizing the at least one carboxylic acid comprised in the mixture obtained from catalytic hydrogenation by adding an aqueous solution comprising hydroxide ions to this mixture to obtain a mixture (Mb) which contains at least one compound having a boiling temperature lower than methanol and lower than water and which is selected from the group consisting of formaldehyde, acetaldehyde, propionaldehyde, methyl formate, formaldehyde dimethyl acetal, acetaldehyde dimethyl acetal, and a mixture of two or more thereof at a given pressure, wherein the molar ratio of hydroxide ions introduced relative to carboxylic acid comprised in the mixture obtained from catalytic hydrogenation is from 0.1 to 10;

(c) separating methanol from mixture (Mb) by
  (c1) separating the at least one compound having a boiling temperature lower than methanol and lower than water from mixture (Mb) by distillation at a distillation pressure of from 0.5 to 2 bar to obtain a mixture (Mb1) and a mixture (Mb2), wherein mixture (Mb1) comprises from 40 to 85 wt.-% methanol and from 10 to 55 wt.-% water and at most 0.1 wt.-% of the at least one compound having a boiling point lower than methanol and water, and wherein mixture (Mb2) comprises from 5 to 50 wt.-% of the at least
  (c2) separating methanol from mixture (Mb1) in at least one distillation stage to obtain a mixture (Mc2i) comprising at least 85 wt.-% of methanol, up to 10 wt.-% of water and 200 ppm or less of carbonyl compounds, and a mixture (Mc2ii) comprising 1,2-dihydroxypropane and at least 90 wt.-% of water, (d) at least partially recycling the methanol obtained from (c2) into (a), the methanol comprising not more than 200 ppm of carbonyl compounds, (e) separating 1,2-dihydroxypropane from mixture (Mc2ii).

19. A process for the purification of methanol, comprising at least partially neutralizing at least one carboxylic acid having from 1 to 3 carbon atoms comprised in a mixture (Ma) by adding a base to mixture (Ma) to obtain a mixture (Mb), said mixture (Ma) further comprising methanol, water and at least one carbonyl compound having from 1 to 3 carbon atoms, wherein the carbonyl compound is an aldehyde or a ketone, said process further comprising separating methanol from mixture (Mb) by distillation.

We claim:

1. A process for the epoxidation of propene, comprising
(a) reacting propene with hydrogen peroxide in the presence of methanol as solvent and a titanium zeolite catalyst and separating propylene oxide from the resulting reaction mixture to obtain a mixture (Ma) comprising methanol, water, at least one carboxylic acid having from 1 to 3 carbon atoms and at least one carbonyl compound having from 1 to 3 carbon atoms, wherein the carbonyl compound is an aldehyde or a ketone;
(b) at least partially neutralizing the at least one carboxylic acid comprised in mixture (Ma) by adding a base to mixture (Ma) to obtain a mixture (Mb);
(c) separating methanol from mixture (Mb) by distillation;
(d) at least partially recycling the methanol obtained from (c) into (a).

2. The process of claim 1, wherein mixture (Ma) comprises from 55 to 85 wt % methanol, from 10 to 40 wt % water, from 0.001 to 0.5 wt % of the at least one carboxylic acid and from 0.01 to 0.2 wt % of the at least one carbonyl compound.

3. The process of claim 1, wherein in (b), an aqueous alkaline solution comprising hydroxide ions is added as base.

4. The process of claim 3, wherein the molar ratio of hydroxide ions introduced in (b) relative to carboxylic acid comprised in (Ma) is from 0.1 to 10.

5. The process of claim 1, wherein in (c), methanol is separated from mixture (Mb) which contains at least one compound having a boiling temperature lower than methanol and lower than water at a given pressure, by (c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt % methanol and from 10 to 55 wt % water and at most 0.1 wt % of the at least one compound having a boiling point lower than methanol and water, and wherein mixture (Mb2) comprises at least 5 wt % of the at least one compound having a boiling point lower than methanol;

(c2) separating methanol from mixture (Mb1) in at least one distillation stage to obtain a mixture (Mc2i) comprising at least 85 wt % of methanol, up to 10 wt % of water and 200 ppm or less of carbonyl compounds, and a mixture (Mc2ii) comprising at least 90 wt % of water.

6. The process of claim 5, wherein the at least one compound having a boiling point lower than methanol is selected from the group consisting of formaldehyde, acetaldehyde, propionaldehyde, methyl formate, formaldehyde dimethyl acetal, acetaldehyde dimethyl acetal, and a mixture of two or more thereof.

7. The process of claim 5, wherein in (c1), distillation is carried out at a pressure of from 0.5 to 5 bar.

8. The process of any of claims 1, wherein mixture (Ma) additionally comprises at least one compound comprising a hydroperoxy group and a hydroxy group, where said hydroxy group is not a portion of said hydroperoxy group.

9. The process of claim 1, wherein prior to (b), mixture (Ma) is subjected to catalytic hydrogenation.

10. The process of claim 9, wherein the hydrogenation catalyst employed for catalytic hydrogenation comprises a catalytically active metal selected from the group consisting of Pd, Pt, Rh, Ir, Os and a mixture of two or more thereof.

11. The process of claim 9, wherein catalytic hydrogenation is carried out at a temperature of from 65 to 85° C. and at a hydrogen partial pressure of from 3 to 20 bar.

12. The process according to claim 11, wherein the hydrogen partial pressure is from 3 to 13 bar.

13. The process of claim 1, wherein the mixture (Ma) additionally comprises 2-hydroperoxypropanol-1, 1-hydroperoxypropanol-2 or a mixture of 2-hydroperoxy-propanol-1 and 1-hydroperoxypropanol-2, and wherein prior to (b), the mixture (Ma) is subjected to a catalytic hydrogenation to give a mixture comprising 1,2-dihydroxypropane.

14. The process of claim 13, wherein in (c), methanol is separated from mixture (Mb) which contains at least one compound having a boiling temperature lower than methanol and lower than water at a given pressure, by (c1) separating the at least one compound having a boiling temperature lower than methanol and lower than water from mixture (Mb) by distillation to obtain a mixture (Mb1) and a mixture (Mb2), wherein mixture (Mb1) comprises from 40 to 85 wt % methanol and from 10 to 55 wt % water and at most 0.1 wt % of the at least one compound having a boiling point lower than methanol and water, and wherein mixture (Mb2) comprises at least 5 wt % of the at least one compound having a boiling point lower than methanol and water;

(c2) separating methanol from mixture (Mb1) in at least one distillation stage to obtain a mixture (Mc2i) comprising at least 85 wt % of methanol, up to 10 wt % of water and 200 ppm or less of carbonyl compounds, and a mixture (Mc2ii) comprising at least 90 wt % of water and 1,2-dihydroxypropane, said process further comprising (e) separating 1,2-dihydroxypropane from mixture (Mc2ii).

15. The process of claim 1, wherein the methanol which is recycled into (a) comprises not more than 200 ppm of carbonyl compounds.

16. The process of claim 9, wherein the catalyst employed for catalytic hydrogenation is at least partially regenerated by treatment with at least one suitable solvent.

17. The process of claim 16, wherein the hydrogenation catalyst employed for catalytic hydrogenation comprises a catalytically active metal selected from the group consisting of Pd, Pt, Rh, Ir, Os and a mixture of two or more thereof.

18. The process of claim 16, wherein the at least one suitable solvent is selected from the group consisting of hydrogen peroxide, methanol, water, propylene oxide, propylene glycol and methoxy propanol.

19. The process of claim 9, wherein the catalyst employed for catalytic hydrogenation is at least partially regenerated by treatment at elevated temperature in the presence of a gas comprising oxygen.

20. The process of claim 19 wherein the hydrogenation catalyst employed for catalytic hydrogenation comprises a catalytically active metal selected from the group consisting of Pd, Pt, Rh, Ir, Os and a mixture of two or more thereof.

21. A process for the epoxidation of propene, comprising
(a) reacting propene with hydrogen peroxide in the presence of methanol as solvent and a titanium zeolite catalyst and separating propylene oxide from the resulting reaction mixture to obtain a mixture (Ma) comprising from 55 to 85 wt % methanol, from 10 to 40 wt % water, from 0.001 to 0.5 wt % of at least one carboxylic acid having from 1 to 3 carbon atoms and from wherein the at least one carboxylic acid is selected from the group consisting of formic acid, acetic acid, propionic acid, and a mixture of two or more thereof, and wherein the at least one carbonyl compound is selected from the group consisting of formaldehyde, acetaldehyde, propionaldehyde, and a mixture of two or more thereof;

said mixture (Ma) further comprising from 0.1 to 1 wt % of 2-hydroperoxypropanol-1, 1-hydroperoxypropanol-2 or a mixture of 2-hydroperoxy-propanol-1 and 1-hydroperoxypropanol-2; and subjecting mixture (Ma) to catalytic hydrogenation at a temperature of from 65 to 85° C. and at a hydrogen partial pressure of from 3 to 20 barz to give a mixture comprising from 0.1 to 1.3 wt % 1,2-dihydroxypropane, the hydrogenation catalyst comprising a catalytically active metal selected from the group consisting of Pd, Pt, Rh, Ir, Os and a mixture of two or more thereof;

(b) at least partially neutralizing the at least one carboxylic acid comprised in the mixture obtained from catalytic hydrogenation by adding an aqueous solution comprising hydroxide ions to this mixture to obtain a mixture (Mb) which contains at least one compound having a boiling temperature lower than methanol and lower than water and which is selected from the group consisting of formaldehyde, acetaldehyde, propionaldehyde, methyl formate, formaldehyde dimethyl acetal, acetaldehyde dimethyl acetal, and a mixture of two or more thereof at a given pressure, wherein the molar ratio of hydroxide ions introduced relative to carboxylic acid comprised in the mixture obtained from catalytic hydrogenation is from 0.1 to 10;

(c) separating methanol from mixture (Mb) by
(c1) separating the at least one compound having a boiling temperature lower than methanol and lower than water from mixture (Mb) by distillation at a distillation pressure of from 0.5 to 2 bar to obtain a mixture (Mb1) and a mixture (Mb2), wherein mixture (Mb1) comprises from 40 to 85 wt % methanol and from 10 to 55 wt % water and at most 0.1 wt % of the at least one compound having a boiling point lower than methanol and water, and wherein mixture (Mb2) comprises from 5 to 50 wt % of methanol and at least 0.1 wt % of the at least one compound having a boiling point lower than methanol and water;

(c2) separating methanol from mixture (Mb1) in at least one distillation stage to obtain a mixture (Mc2i) comprising at least 85 wt % of methanol, up to 10 wt % of water and 200 ppm or less of carbonyl compounds, and a mixture (Mc2ii) comprising 1,2-dihydroxypropane and at least 90 wt % of water, (d) at least partially recycling the methanol obtained from (c2) into (a), the methanol comprising not more than 200 ppm of carbonyl compounds, (e) separating 1,2-dihydroxypropane from mixture (Mc2ii).

22. The process according to claim 21, wherein the hydrogen partial pressure of (a) is from 3 to 13 bar.

* * * * *

UNITED STATES PATENT AND TRADEMARK OFFICE
CERTIFICATE OF CORRECTION

PATENT NO. : 7,786,317 B2  
APPLICATION NO. : 12/159404  
DATED : August 31, 2010  
INVENTOR(S) : Hans-Georg Goebbel et al.

Page 1 of 1

It is certified that error appears in the above-identified patent and that said Letters Patent is hereby corrected as shown below:

Please add the following three names to the list of inventors on the Title page, item (75):
Ekkehard Schwab, Till Gerlach and Georg Krug.

The correct inventorship of the above-identified application is as listed below:

Hans-Georg Goebbel  
Peter Bassler  
Joaquim Teles  
Peter Rudolph  
Ulrich Muller  
Anna Forlin  
Malte Schulz  
Meinolf Weidenbach  
Ekkehard Schwab  
Till Gerlach  
Georg Krug Signed and Sealed this  
Eighteenth Day of June, 2013

Teresa Stanek Rea  
*Acting Director of the United States Patent and Trademark Office*